(12) United States Patent
Sundberg et al.

(10) Patent No.: US 8,277,759 B2
(45) Date of Patent: Oct. 2, 2012

(54) MICROFLUIDIC FLOW CELL

(75) Inventors: Scott O. Sundberg, Holladay, UT (US); Carl T. Wittner, Salt Lake City, UT (US); Bruce K. Gale, Taylorsville, UT (US)

(73) Assignee: The University of Utah Research Foundation, Salt Lake City, UT (US)

( * ) Notice: Subject to any disclaimer, the term of this patent is extended or adjusted under 35 U.S.C. 154(b) by 113 days.

(21) Appl. No.: 12/920,577

(22) PCT Filed: Mar. 3, 2009

(86) PCT No.: PCT/US2009/035859
§ 371 (c)(1),
(2), (4) Date: Dec. 6, 2010

(87) PCT Pub. No.: WO2009/111461
PCT Pub. Date: Sep. 11, 2009

(65) Prior Publication Data
US 2011/0104688 A1    May 5, 2011

Related U.S. Application Data

(60) Provisional application No. 61/033,724, filed on Mar. 4, 2008.

(51) Int. Cl.
*G01N 21/07* (2006.01)
*G01N 21/01* (2006.01)
*C12Q 1/68* (2006.01)

(52) U.S. Cl. ......... 422/503; 422/504; 435/6; 435/287.2; 216/52; 264/400; 264/293

(58) Field of Classification Search .................. None
See application file for complete search history.

(56) References Cited

U.S. PATENT DOCUMENTS

| | | | |
|---|---|---|---|
| 5,693,233 A | 12/1997 | Schembri | |
| 6,527,432 B2 | 3/2003 | Kellogg | |
| 6,632,655 B1* | 10/2003 | Mehta et al. | 506/14 |
| 2003/0053934 A1 | 3/2003 | Andersson | |
| 2004/0063151 A1* | 4/2004 | Beebe et al. | 435/7.1 |
| 2007/0035818 A1* | 2/2007 | Bahatt et al. | 359/366 |
| 2008/0003145 A1* | 1/2008 | Nurse et al. | 422/99 |
| 2011/0020947 A1* | 1/2011 | Bedingham et al. | 436/174 |

FOREIGN PATENT DOCUMENTS

JP    2006317467    11/2006

* cited by examiner

*Primary Examiner* — In Suk Bullock
*Assistant Examiner* — Timothy G Kingan
(74) *Attorney, Agent, or Firm* — Workman Nydegger

(57) ABSTRACT

A microfluidic flow cell having a body with a fluid transport channel disposed therein, the fluid transport channel having a proximal end and a distal end defining a fluid flow path, a fluid inlet port disposed at the proximal end of the fluid transport channel at a central portion of the body and an outlet port disposed at the distal end of the fluid transport channel at an outer portion of the body, and a plurality sample wells disposed in the fluid transport channel substantially perpendicular to the fluid flow path in the fluid transport channel. The microfluidic flow cell may have hundreds or thousands of individual, sub-microliter sample wells. The microfluidic flow cell can be filled by applying a flowable liquid to the inlet port and spinning the flow cell to cause fluid to flow into fluid transport channel. The microfluidic flow cells described herein can be used in a variety of applications where small sample size and/or a large number of replicates are desirable.

47 Claims, 6 Drawing Sheets

MICROFLUIDIC FLOW CELL

CROSS-REFERENCE TO RELATED APPLICATION

This application claims priority to and the benefit of U.S. Provisional Patent Application Ser. No. 61/033,724 filed Mar. 4, 2008 to Sundberg et al. entitled "DIGITAL PCR FOR DIRECT HAPLOTYPING IN A MICROFLUIDIC FLOW CELL BY MELTING ANALYSIS," the entirety of which is incorporated herein by specific reference.

BACKGROUND OF THE INVENTION

1. The Field of the Invention

The present invention relates to microfluidic devices having large numbers of small (between about 1 nl and about 100 nl) sample wells.

2. The Relevant Technology

The term "digital PCR" was first coined in 1999 by Burt Vogelstein (Vogelstein and Kinzler 1999). Limiting dilution was used to detect a minor fraction of altered DNA by diluting to the point of having only one DNA template in a given reaction volume. PCR was then run with molecular beacon probes in solution. Once amplified, the reaction volumes were fluorescently analyzed; wild type and mutated DNA were then quantified by relying on binary positive/negative calls.

Recently the concept of digital PCR has been miniaturized using microfluidics to limit the amount of DNA template rather than dilutions. One such application presented was multigene analysis of environmental bacteria using multiplex digital PCR (Ottesen et al. 2006). Quantitative population analysis of transcription factor expression has also been shown (Warren et al. 2006). Each of these microfluidic applications uses Fluidigm's Digital Array chip. Fluid is distributed into parallel dead-end channels using pneumatic pressure. A comb valve is then actuated, deflecting a membrane down to section off 1,200 isolated reaction chambers of 10 nl each. This chip is then thermocycled and analyzed using a microarray scanner.

Ottesen et al. and Warren et al.'s research was used for absolute quantification of sample. However, downsides do exist to their micro fluidic platform and detection scheme. One downside is the high cost for manufacturing the microchips and the expensive equipment required to valve their system to create individual wells. Another downside is the multicolor requirement needed with labeled probes.

DNA melting analysis as a complement to PCR was introduced in 1997 (Ririe et al. 1997). A dye is included in the PCR that fluoresces in the presence of double-stranded DNA, but not single-stranded DNA. After amplification, fluorescence is monitored as the double-stranded DNA product is slowly heated. When the double helix melts, fluorescence rapidly decreases. The negative first derivative of fluorescence with respect to temperature shows the melting temperature (Tm) as maxima. Recent advances in melting instrumentation (Herrmann et al. 2006) and saturating DNA dyes (Wittwer et al. 2003) allow detection of single nucleotide polymorphisms (SNPs). If the change is heterozygous, DNA heteroduplexes alter the shape of the melting curve (Reed et al. 2004). If the change is homozygous, the absolute temperature of the melting transition shifts (Liew et al, 2004). DNA melting analysis, when compared to existing PCR analytical techniques, is advantageous because it is less complicated, faster (less than 20 minutes for PCR and analysis), and prevents contamination of the sample and environment due to its "closed-tube" format (Zhou et al. 2004). The specific dye used determines the capabilities of the method; LCGreen® Plus detects homozygous and heterozygous sequences well and does not inhibit PCR (Wittwer et al. 2003).

Analysis of the melting transition is often sufficient for genotyping. However, unlabeled probes combined with asymmetric PCR provide even greater specificity over a smaller region, which may be necessary for variant discrimination (Zhou et al. 2005) and is commonly believed to be essential for clinical assays. A recent publication has demonstrated that DNA melting analysis is capable of being miniaturized, thus providing initial results for a microarray chip platform, reducing reagent costs (Sundberg et al. 2007).

BRIEF SUMMARY OF THE INVENTION

The present invention encompasses novel microfluidic flow cells. The microfluidic flow cells of the present invention include a fluid transport channel and a plurality of sample wells disposed in the fluid transport channel. A typical microfluidic flow cell as disclosed herein may have hundreds or thousands of individual, sub-microliter sample wells. The microfluidic flow cells described herein can be used in a variety of applications where small sample size and/or a large number of replicates are desirable.

In one embodiment, a microfluidic flow cell is disclosed. The microfluidic flow cell can include a body having a fluid transport channel disposed therein, the fluid transport channel having a proximal end and a distal end defining a fluid flow path, a fluid inlet port disposed at the proximal end of the fluid transport channel at a central portion of the body and an outlet port disposed at the distal end of the fluid transport channel at an outer portion of the body, and a plurality of sample wells disposed in the fluid transport channel substantially perpendicular to the fluid flow path in the fluid transport channel such that a liquid medium flowing through the fluid transport channel will flow into at least a first sample well with an excess of the liquid medium flowing into at least a second sample well.

In one embodiment, the sample wells disposed in the fluid flow path can have a volume between about 1 nl and about 100 nl, or preferably a volume between about 10 nl and about 80 nl, or more preferably a volume between about 20 nl and about 50 nl.

In another embodiment of a microfluidic flow cell can include a disc-shaped body configured for spinning about a central axis. The body can further include at least one fluid inlet port situated toward a center portion of the disc and at least one fluid outlet port situated toward an outer edge of the disc, at least one fluid transport channel defining a fluid flow path in the body, the fluid transport channel being disposed in the body such that it is in fluid communication with a fluid inlet port and a fluid outlet port, and a plurality of sample wells disposed in the at least one fluid transport channel such that the sample wells are substantially perpendicular to the fluid flow path. One consequence of positioning the fluid inlet port toward the center of the disc and the fluid outlet port toward the outer edge of the disc with the fluid transport channel running between the inlet and outlet ports is that a fluid applied at the inlet port will flow through the body along the fluid path toward the outlet port in response to spinning the disc-shaped body about the central axis.

In one embodiment, the present invention can include a microfluidic flow cell that includes a plurality of inlet ports situated toward the center of the disc, a plurality of outlet ports situated toward the outer edge of the disc, and a plurality of fluid transport channels for transporting a flowable fluid with each channel being connected to one inlet port and one outlet port.

In one embodiment a method for filling a microfluidic flow cell is described. The method can include providing a microfluidic flow cell as described above, applying a volume of a flowable fluid to the fluid inlet port, and flowing the flowable fluid through the fluid transport channel toward the fluid outlet port such that the flowable fluid will flow into at least a first sample well with an excess of the flowable fluid flowing into at least a second sample well.

In one embodiment, the fluid can be flowed into the microfluidic flow cell by spinning the flow cell about its central axis in a centrifuge so as to cause the flowable fluid to flow from the fluid inlet port, through the fluid transport channel, and toward the fluid outlet port. In one embodiment, the spinning can include spinning the flow cell at a rate between about 500 rpm and about 10,000 rpm, or preferably a rate between about 2000 rpm and about 8000 rpm, or more preferably a rate between about 3000 rpm and about 5000 rpm.

In one embodiment, the present invention includes a method for manufacturing a microfluidic flow cell. The method includes providing a fluid transport layer, wherein the providing includes forming a fluid transport channel defining a fluid flow path in the fluid transport layer, the fluid transport channel having a proximal end at a central portion of the fluid transport layer and a distal end at an outer portion of the fluid transport layer, forming a plurality of sample wells in the fluid transport channel, the plurality of sample wells being substantially perpendicular to the fluid flow path in the fluid transport channel, and sealing the fluid transport layer with at least one outer layer.

Suitable examples of techniques for forming the fluid transport channel and the samples wells include, but are not limited to, at least one of xurography, etching, laser cutting, stamping, hot embossing, injection molding, or micro machining.

In one embodiment, the fluid transport layer is formed from a polymeric, thermoplastic material. In another embodiment, the fluid transport layer is formed from a glass material. In yet another embodiment, the fluid transport layer is formed from an inert material. In still yet another embodiment, the fluid transport layer is formed from a material having an affinity for DNA, RNA, and/or protein.

In one embodiment, the method for manufacturing a microfluidic flow cell further includes disposing an outer layer over the fluid transport layer, the outer layer including at least inlet and outlet ports that are in fluid communication with the fluid transport channel.

In another embodiment, the method for manufacturing a microfluidic flow cell further includes disposing the fluid transport layer between the first and second outer layers, the first and second outer layers including at least inlet and outlet ports that are in fluid communication with the fluid transport channel.

In one embodiment, the present invention includes a method for DNA or RNA quantification. The method can include (1) providing a microfluidic flow cell as described above, (2) loading the plurality of sample wells in the microfluidic cell with a reaction mixture, the reaction mixture including a nucleic acid template, a plurality of primer strands for amplifying a sequence of interest, and means for amplifying the nucleic acid template, (3) amplifying the nucleic acid template to generate an amplified product therefrom, (4) detecting the presence or absence of the amplified product in a plurality of wells, and (5) quantifying the amount of the nucleic acid template amplified.

Suitable examples of means for amplifying the nucleic acid template include, but are not limited to, at least one of polymerase chain reaction (PCR), ligase chain reaction (LCR), transcription mediated amplification (TMA), rolling circle amplification (RCA), strand displacement amplification (SDA), or loop-mediated amplification (LAMP).

In one embodiment, the plurality of primer strands includes at least one of a forward primer or a reverse primer for amplifying the sequence of interest.

In one embodiment, the method further includes sealing the fluid transport channel so as to prevent evaporation of the fluid in the sample wells.

Preferably, the concentration of nucleic acid template is selected such that the number of copies of the nucleic acid template in the reaction mixture that is loaded into the microfluidic flow cell is less than the number of sample wells so that, on average, the bulk of the sample wells have either zero copies of the nucleic acid template or one copy of the nucleic acid template with a small number of cells having two or more copies of the nucleic acid template. As such, the nucleic acid template is provided at a concentration such that the plurality of sample wells contain an average of about 0.1 copies of the nucleic acid template per sample well to about 1 copy of the nucleic acid template per sample well. More preferably, the concentration of the nucleic acid template is such that the plurality of sample wells contain an average of about 0.2 copies of the nucleic acid template per sample well to about 0.8 copies of the nucleic acid template per sample well. Most preferably, the concentration of the nucleic acid template is such that the plurality of sample wells contain an average of about 0.3 copies of the nucleic acid template per sample well to about 0.5 copies of nucleic acid template per sample well.

In one embodiment, the nucleic acid template can be from a diploid organism. In such a situation, the nucleic acid template is preferably provided at a concentration such that the plurality of sample wells contain no more than one copy of the organism's two copies of the sequence of interest.

In one embodiment, the method further includes providing a microfluidic flow cell formed from a material having an affinity for the nucleic acid template such that the nucleic acid template is progressively diluted as it flows through the fluid transport channel from the inlet port toward the outlet port, and plotting a frequency of sample wells having amplified product versus sample wells having no amplified product as a function of distance along the fluid transport channel so as to find a subset of sample wells having a concentration of the nucleic acid template usable for DNA or RNA quantification.

Suitable examples of applications where DNA or RNA quantification can be used with the method described herein include, but are not limited to, at least one of cancer detection, cancer therapy response monitoring, quantification of viral load, prenatal genetic testing, or direct haplotyping.

In one embodiment, the DNA quantification can further include performing melting analysis on the amplified product by raising the temperature of the microfluidic flow cell and the contents therein, and monitoring the absorbance and/or fluorescence in each of the sample wells while raising the temperature to generate a melting profile for the amplified product, wherein a change in absorbance and/or fluorescence indicates denaturation of double stranded nucleic acids.

In one embodiment, the method can further include analyzing the results of the melting analysis, wherein a shift in the melting profile of the amplified product indicates the presence of sequence variants in the nucleic acid template.

In one embodiment, DNA melting analysis can be facilitated by including one or more DNA probe strands that are capable of forming a double stranded DNA structure with the sequence of interest and/or a fluorescent dye that fluoresces in the presence of double-stranded DNA.

In one embodiment, the method can further include providing a light source that can be positioned and timed for providing light at a fluorescence excitation wavelength to at least one sample well, flashing the light source at the fluorescence excitation wavelength so as to excite fluorescent emission from the fluorescent dye in the at least one sample well, and detecting the fluorescent emission from the fluorescent dye in the at least one sample well using a positionable detector means, wherein flashing the light source prevents photobleaching of the fluorescent dye in the sample well.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction

The present invention encompasses novel microfluidic flow cells. The microfluidic flow cells of the present invention include a fluid transport channel and a plurality of sample wells disposed in the fluid transport channel. A typical microfluidic flow cell as disclosed herein may have hundreds or thousands of individual, sub-microliter sample wells. The microfluidic flow cells described herein can be used in a variety of applications where small sample size and/or a large number of replicates are desirable.

II. Microfluidic Flow Cell

Figure 1A:
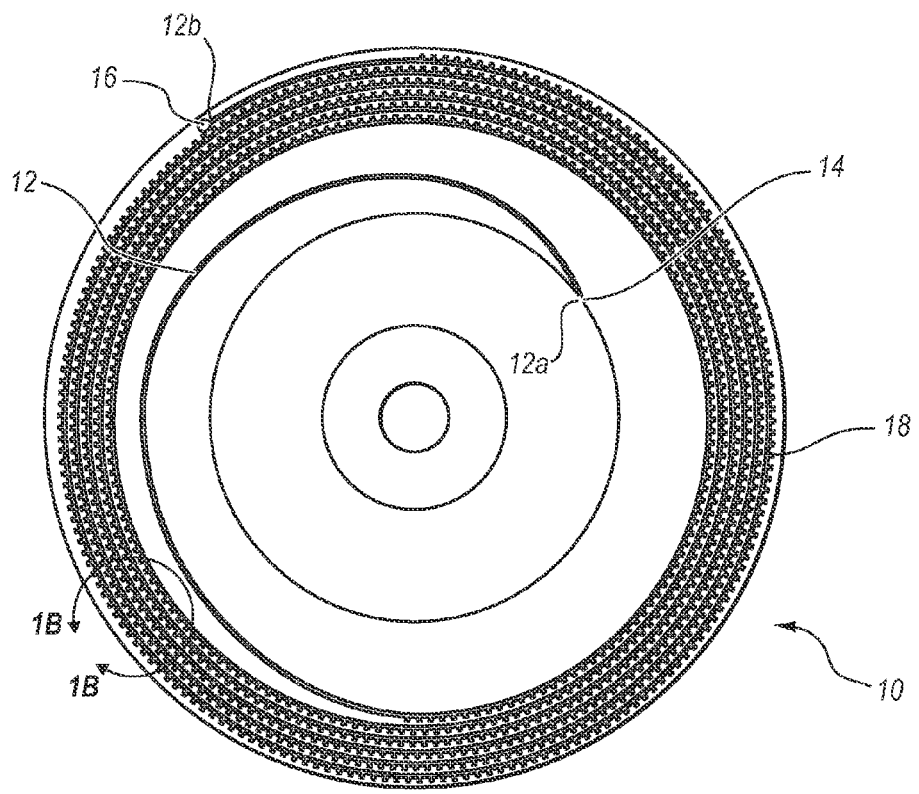
FIG. 1A illustrates a disc-shaped microfluidic cell according to one embodiment of the present invention.

In one embodiment, a microfluidic flow cell is disclosed. FIG. 1A illustrates a disc-shaped microfluidic flow cell 10 according to one embodiment of the present invention. The microfluidic flow cell 10 can include a disc-shaped body having a fluid transport channel 12 disposed therein, the fluid transport channel having a proximal end 12a and a distal end 12b defining a fluid flow path (depicted schematically by arrow 120 in FIG. 1C), a fluid inlet port 14 disposed at the proximal end 12a of the fluid transport channel at a central portion of the body and an outlet port 16 disposed at the distal end 12b of the fluid transport channel at an outer portion of the body, and a plurality of sample wells 18 disposed in the fluid transport channel 12.

Outlet port 16 can allow air or excess fluid to escape from the fluid transport channel 12 when fluid is loaded into the microfluidic flow cell 10. As such, outlet port 16 can include an opening at the distal end 12b of the fluid transport channel 12 that allows air and liquid to escape. However, outlet port 16 can also include a reservoir or another means for trapping excess fluid while permitting air to escape.

In one embodiment, the sample wells 18 disposed in the fluid transport channel 12 can have a volume between about 1 nl and about 100 nl, or preferably a volume between about 10 nl and about 80 nl, or more preferably a volume between about 20 nl and about 50 nl.

Figure 1B:
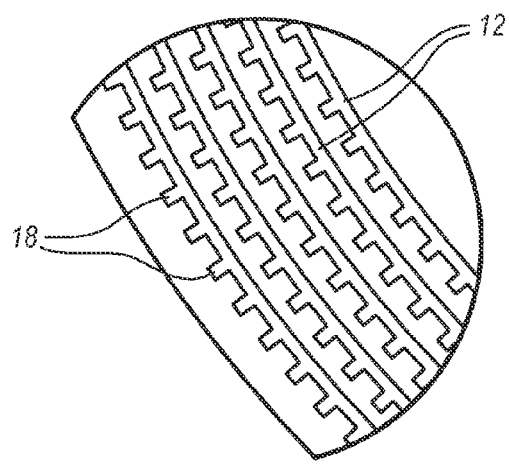
FIG. 1B illustrates a detailed view of a portion of the microfluidic cell depicted in FIG. 1A.
Figure 1C:
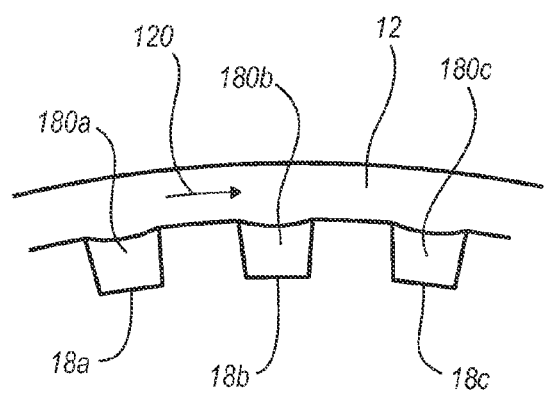
FIG. 1C illustrates detailed view of a portion of the microfluidic cell depicted in FIG. 1A in which the sample cells are filled with a fluid.

FIGS. 1B and 1C illustrate detailed views of a portion of the microfluidic cell depicted in FIG. 1A. As depicted in FIGS. 1A, 1B, and 1C the plurality of sample wells 18 are disposed substantially perpendicular to the fluid flow path in the fluid transport channel 12.

In one embodiment, liquid media (i.e., aqueous and non-aqueous fluids) can be loaded into the disc-shaped microfluidic cell 10 such as the one depicted in FIGS. 1A-1C by applying a volume of a flowable fluid to the fluid inlet port 14, and flowing the flowable fluid through the fluid transport channel 12 toward the outlet port 16 such that the flowable fluid will flow into at least a first sample well with an excess of the flowable fluid flowing into at least a second sample well.

In a preferred embodiment, the fluid can be flowed into the disc-shaped microfluidic cell 10 by spinning the flow cell about its central axis in a centrifuge so as to cause the flowable fluid to flow from the fluid inlet port 14, through the fluid transport channel 12, and toward the fluid outlet port 16. As the liquid medium flows through the fluid transport channel 12 under centrifugation, the fluid will flow into at least a first sample well 18a with an excess of the fluid flowing into at least a second sample well 18b or a third sample well 18c. The effect of this is illustrated in FIG. 1C, which depicts three adjacent sample wells 18a-18c in transport channel 12. Sample wells 18a-18c are each filled with fluid 180a-180c. Interestingly, centrifugation can leave the fluid transport 12 depicted in FIG. 1C free of excess fluid (i.e., the excess flows toward outlet port 16) while filling adjacent sample wells 18a-18c. One consequence of this is that adjacent sample wells (e.g., 18a and 18b) are effectively isolated from one another even though they were filled from the same bolus of fluid that was applied to inlet port 14.

In one embodiment, the spinning (i.e., centrifugation) can include spinning the flow cell at a rate between about 500 rpm and about 10,000 rpm, or preferably a rate between about 2000 rpm and about 8000 rpm, or more preferably a rate between about 3000 rpm and about 5000 rpm.

Figure 2A:
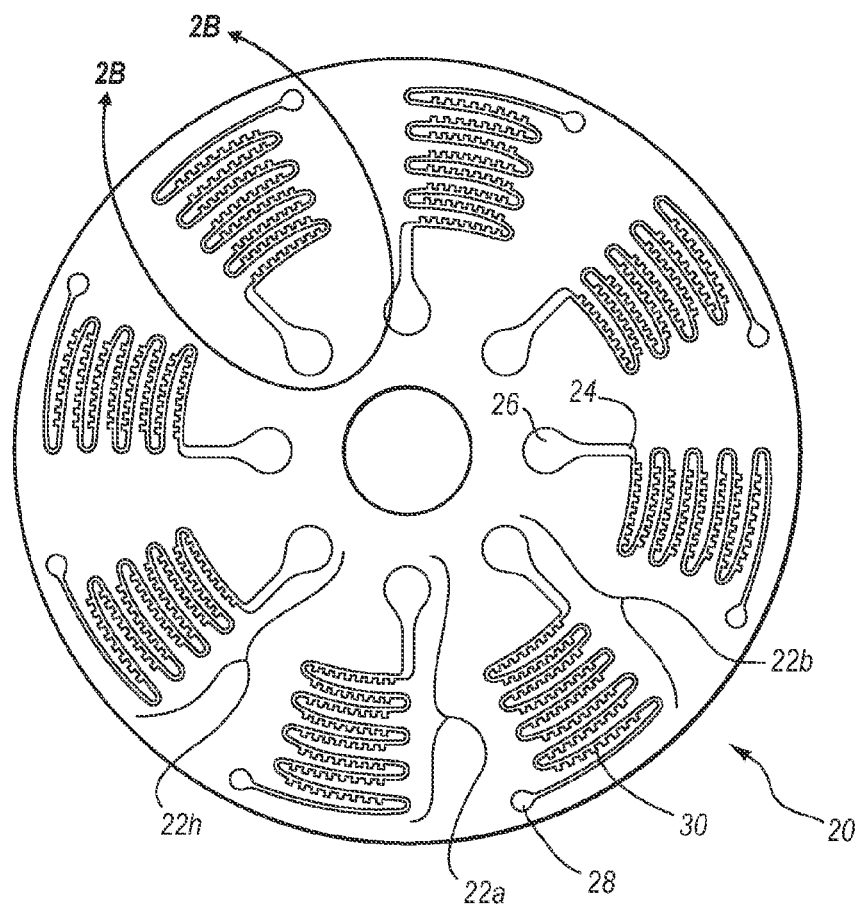
FIG. 2A illustrates a disc-shaped microfluidic cell according to another embodiment of the present invention.
Figure 2B:
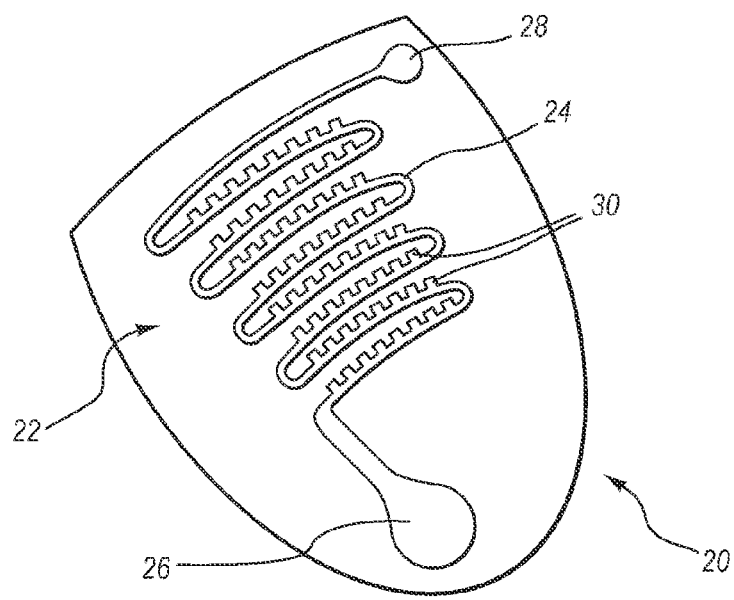
FIG. 2B illustrates a detailed view of a portion of the microfluidic cell depicted in FIG. 2A.

FIGS. 2A and 2B depict an alternative embodiment of the present invention wherein the disc-shaped microfluidic flow cell 20 includes a plurality of separate flow paths 22a-22h. Each flow path 22 includes a fluid transport channel 24 that is in fluid communication with an inlet port 26 situated toward the center of the disc 20 and an outlet port 28 situated toward the outer edge of the disc 20. In addition, each fluid transport channel 24 includes a plurality of sample wells that are disposed in the fluid transport channel 24 substantially perpendicular to the direction of fluid flow in the fluid transport channel 24.

II. Methods for Manufacturing a Microfluidic Flow Cell

In one embodiment, a method for manufacturing a microfluidic flow cell is disclosed. The method can include providing a fluid transport layer, wherein the providing can include forming a fluid transport channel defining a fluid flow path in the fluid transport layer, the fluid transport channel having a proximal end at a central portion of the fluid transport layer and a distal end at an outer portion of the fluid transport layer; forming a plurality sample wells in the fluid transport channel, the plurality sample wells being substantially perpendicular to the fluid flow path in the fluid transport channel, and sealing the fluid transport layer with at least one outer layer.

Suitable examples of techniques for forming the fluid transport channel and the samples wells include, but are not limited to, at least one of xurography, lithography and etching, laser cutting, stamping, hot embossing, injection molding, or micro machining.

Xurography, which literally translates to razor writing, uses a cutting plotter traditionally used in the sign industry for cutting graphics in adhesive vinyl films to cut microfluidic structures, with 10 µm resolution, from adhesive films. These structures can be cut and laminated or adhered into multi-layered microfluidic devices. Xurography does not require a clean room or caustic chemicals, as compared to other prototyping techniques.

Lithography and etching are commonly used to produce microstructures in a variety of substrates. In a typical process, a masking agent is applied to the surface of a material using lithography. The portions of the surface that are not protected by the masking agent are then chemically etched using an etchant. Lithography and etching can produce highly detailed structures.

Laser cutting typically involves the use of a computer-controlled laser to cut or ablate structures out of a material. Laser cutting can produce highly detailed structures.

Stamping processes such as dye cutting, hot-pressing and injection molding can be used to form a variety of shapes in a variety of materials. Dye-cutting can be used to repeatedly cut detailed structures out of a variety of materials. Hot-embossing can be used to impress a variety of shapes into a variety of materials. Injection molding can be used to form a variety of shapes from a variety of materials including polymers and metals.

Micro machining is similar to conventional machining except micro machining can typically be used to machine micron-scale structures in a variety of materials.

In one embodiment, the fluid transport layer is formed from a polymeric, thermoplastic material. In another embodiment, the fluid transport layer is formed from a glass material. In yet another embodiment, the fluid transport layer is formed from an inert material. In still yet another embodiment, the fluid transport layer is formed from a material having an affinity for DNA, RNA, and/or protein. For instance, the inventors have found that microfluidic flow cells fabricated from PETG (i.e., glycol-modified polyethylene terephthalate) have an intrinsic affinity for DNA. While this may be disadvantageous in some cases, the inventors have found that it can be advantageous for some PCR reactions because some of the nucleic acid template appears to get "stuck" as it flows through the flow cell, so that the effective concentration of the template DNA decreases along the path of fluid flow. When working with template DNA of unknown concentration, this means that it is likely that at least a subset of sample wells along the flow path will have a DNA concentration that is sufficiently low to allow for DNA quantification.

In one embodiment, the method for manufacturing a microfluidic flow cell further includes disposing an outer layer over the fluid transport layer, the outer layer including at least inlet and outlet ports that are in fluid communication with the fluid transport channel.

In another embodiment, the method for manufacturing a microfluidic flow cell further includes disposing the fluid transport layer between the first and second outer layers, the first and second outer layers including at least inlet and outlet ports that are in fluid communication with the fluid transport channel.

Figure 3:
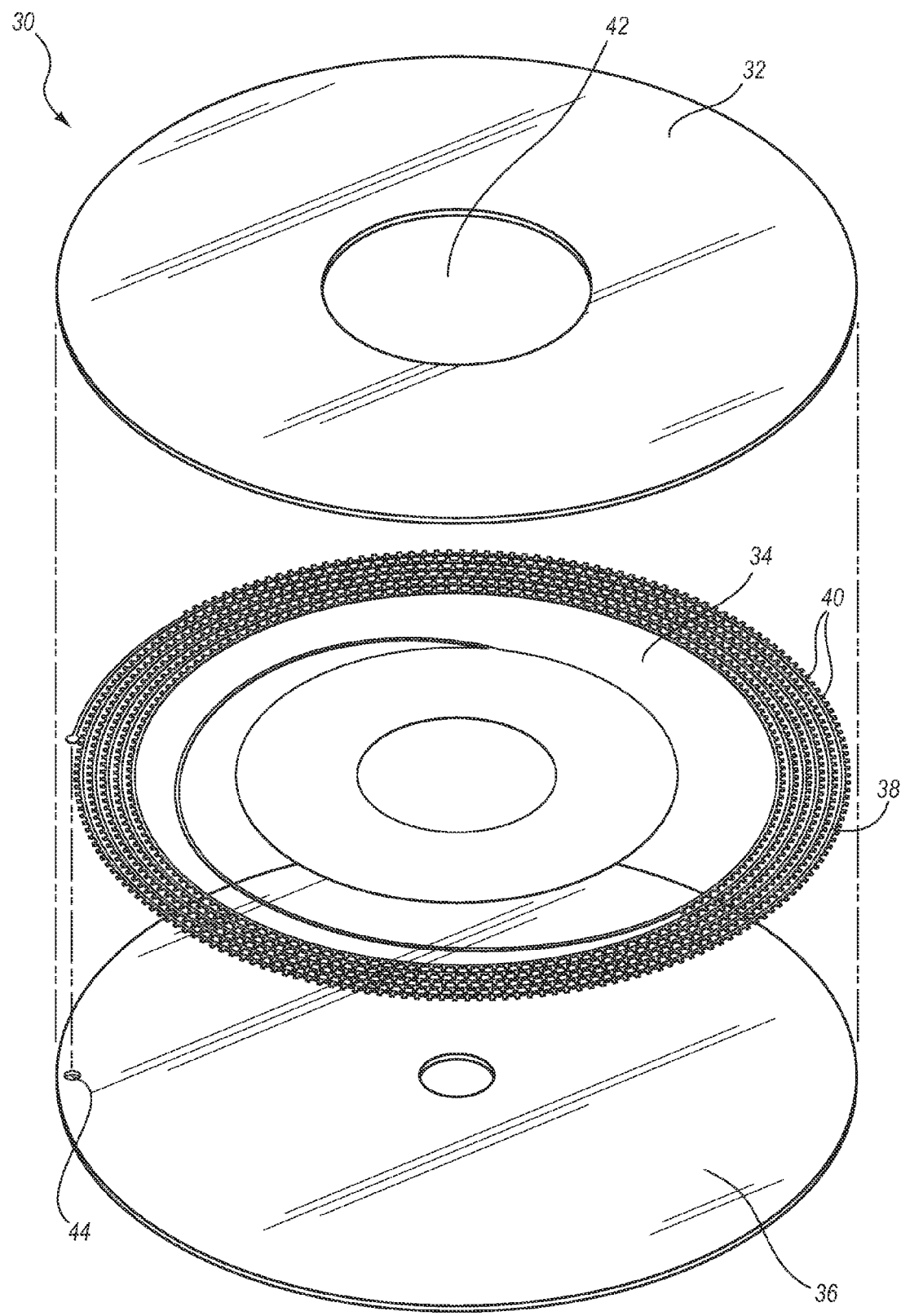
FIG. 3 illustrates an assembly techniques for a disc-shaped microfluidic cell.
Figure 4:
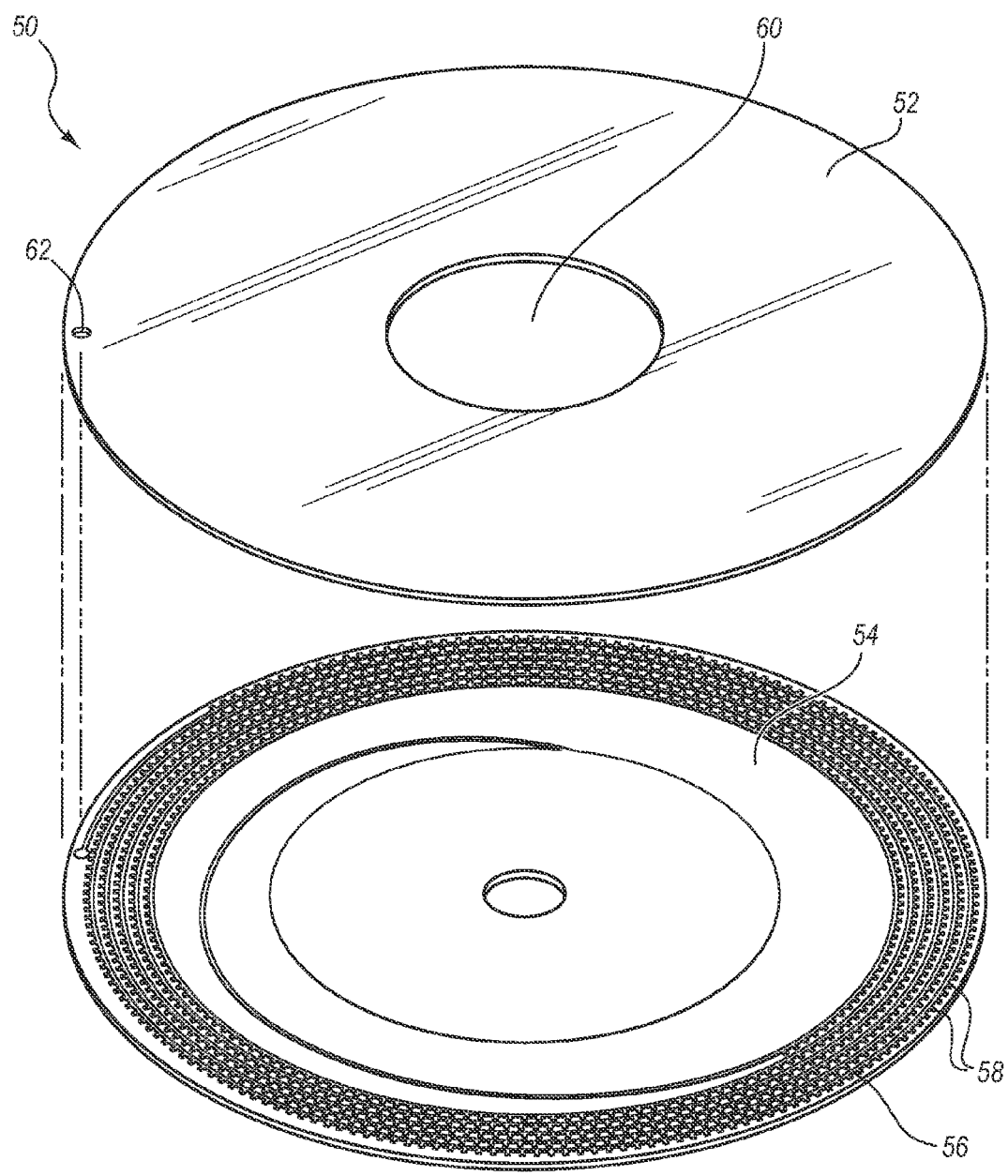
FIG. 4 illustrates another assembly techniques for a disc-shaped microfluidic cell.

FIGS. 3 and 4 show the assembly of disc-shaped microfluidic cells. FIG. 3 illustrates a microfluidic cell 30 that includes three layers—a fluid transport layer 34 and two outer layers 32 and 36. The fluid transport layer includes a fluid transport channel 38 and a plurality of sample wells 40 formed in the fluid transport channel 38. Outer layer 32 includes an inlet port 42 that is in fluid communication with the fluid transport channel 38. Outer layer 36 includes an outlet port 44 that is in fluid communication with the fluid transport channel 38. Microfluidic cell 30 is assembled by disposing fluid transport layer 34 between outer layers 32 and 36 and fusing the layers together.

FIG. 4 illustrates a microfluidic cell 50 that includes two layers—a fluid transport layer 54 and an outer layer 52. The fluid transport layer includes a fluid transport channel 56 and a plurality of sample wells 58 formed in the fluid transport channel 56. Outer layer 52 includes an inlet port 60 that is in fluid communication with the fluid transport channel 56. In the embodiment depicted in FIG. 4, outlet port 62 is disposed in the fluid transport layer 54. One will appreciate, however, that outlet port 62 could also be included in outer layer 52. Microfluidic cell 50 is assembled by disposing outer layer 52 over fluid transport layer 54 and fusing the layers together.

III. Methods Using a Microfluidic Flow Cell

In one embodiment, a method for DNA or RNA quantification is disclosed. The method can include (1) providing a microfluidic flow cell as described above, (2) loading the plurality of sample wells in the microfluidic cell with a reaction mixture, the reaction mixture including a nucleic acid template, a plurality of primer strands for amplifying a sequence of interest, and means for amplifying the nucleic acid template, (3) amplifying the nucleic acid template to generate an amplified product therefrom, (4) detecting the presence or absence of the amplified product in a plurality of wells, and (5) quantifying the amount of the nucleic acid template amplified.

Suitable examples of means for amplifying the nucleic acid template include, but are not limited to, at least one of polymerase chain reaction (PCR), ligase chain reaction (LCR), transcription mediated amplification (TMA), rolling circle amplification (RCA), strand displacement amplification (SDA), or loop-mediated amplification (LAMP).

The polymerase chain reaction (PCR) is a fast and inexpensive technique used to "amplify" (i.e., copy) small segments of DNA or RNA. Because significant amounts of a sample of DNA or RNA are necessary for molecular and genetic analyses, studies of isolated pieces of DNA or RNA are greatly facilitated by PCR amplification.

To amplify a segment of DNA using PCR, the sample is first heated so the template DNA denatures, or separates into two pieces of single-stranded DNA. The temperature is then lowered so that short primer strands can anneal to a sequence of interest. Next, a thermostable DNA polymerase (e.g., Taq polymerase or Pfu polymerase) synthesizes two new strands of DNA, starting at the primers and using the original strands as templates. This process results in the duplication of the original DNA, with each of the new molecules containing one old and one new strand of DNA. Then each of these strands can be used to create two new copies, and so on, and so on. The cycle of denaturing and synthesizing new DNA is repeated as many as 30 or 40 times, leading to an exponential increase in the number of copies of the original DNA sequence of interest. To amplify a segment of RNA, it is first reverse transcribed into cDNA using a reverse transcriptase, after which PCR is performed.

The entire cycling process of PCR can be automated and can be completed in just a few hours or less. It is directed by a machine called a thermocycler, which is programmed to alter the temperature of the reaction to allow cycles of DNA denaturation, annealing, and synthesis.

The ligase chain reaction (LCR) is a method of DNA amplification. While the better-known PCR carries out the amplification by polymerizing nucleotides, LCR instead amplifies the nucleic acid used as the probe. For each of the two DNA strands, two partial probes are ligated to form the actual one. Each cycle results in a doubling of the target nucleic acid molecule. A key advantage of LCR is increased specificity as compared to PCR. It has been widely used for the detection of single base mutations, as in genetic diseases. Additional discussion regarding the ligase chain reaction can be found in "Ligase Chain Reaction (LCR)—Overview and Applications" by Weidmann et al. *Genome Res.* 1994 3: S51-S64.

Transcription-mediated amplification (TMA) uses two primers and two enzymes: RNA polymerase and reverse transcriptase. One of the primers contains a promoter sequence for RNA polymerase. In the first step of amplification, the promoter-primer hybridizes to the target RNA at a defined site. Reverse transcriptase creates a DNA copy of the target RNA by extension from the 3' end of the promoter-primer. The RNA in the resulting RNA:DNA duplex is degraded by the RNAse H activities of the reverse transcriptase. A second primer then binds to the DNA copy. A new strand of DNA is synthesized from the end of the primer by reverse transcriptase creating a double stranded DNA molecule. RNA polymerase recognizes the promoter sequence in the DNA template and initiates transcription. Each of the newly synthesized RNA amplicons re-enters the TMA process and serves as a template for a new round of replication leading to an exponential expansion of the RNA amplicon. Since each of the DNA templates can make 100-1000 copies of RNA amplicon, this expansion can result in the production of 10 billion amplicons in less than one hour. The entire process is autocatalytic and is performed at a single temperature. Additional discussion regarding transcription-mediated amplification can be found in "Gen-Probe Transcription-Mediated Amplification: System Principles" by Craig S. Hill, Gen-Probe, Inc.

Rolling circle amplification (RCA) can be used to amplify vector DNA such as M13 or plasmid DNA from single colonies or plaques. Using random primers and φ29 DNA polymerase, circular DNA templates can be amplified 10,000-fold in a few hours. This procedure removes the need for lengthy growth periods and traditional DNA isolation methods. Reaction products can be used directly for DNA sequencing after phosphatase treatment to inactivate unincorporated nucleotides. Amplified products can also be used for in vitro cloning, library construction, and other molecular biology applications. Additional discussion regarding rolling circle amplification can be found in "Rapid Amplification of Plasmid and Phage DNA Using Phi29 DNA Polymerase and Multiply-Primed Rolling Circle Amplification" by Dean et al. *Genome Res.* 2001 11: 1095-1099.

Strand displacement amplification (SDA) is an isothermal, in vitro nucleic acid amplification technique based upon the ability of HincII to nick the unmodified strand of a hemiphosphorothioate form of its recognition site, and the ability of exonuclease deficient klenow (exo-klenow) to extend the 3'-end at the nick and displace the downstream DNA strand. Exponential amplification results from coupling sense and antisense reactions in which strands displaced from a sense reaction serve as target for an antisense reaction and vice versa. Additional discussion regarding strand displacement amplification can be found in U.S. Pat. No. 5,712,124 to Walker et al. and in "Strand displacement amplification—an isothermal, in vitro DNA amplification technique" by Walker et al. *Nucleic Acids Res.* 1992 Apr. 11; 20(7): 1691-1696.

Loop mediated isothermal amplification (LAMP) is a gene amplification technique that can be completed in less than 1 h under isothermal conditions. LAMP employs a set of six specially designed primers spanning eight distinct sequences of a target gene and by incubating all the reagents in a single tube. Gene amplification products can be detected by agarose gel electrophoresis as well as by real-time monitoring in an inexpensive turbidimeter. Gene copy number can also be quantified with the help of a standard curve generated from different concentrations of gene copy number plotted against time of positivity with the help of a real-time turbidimeter. Alternatively, gene amplification can be visualized by the naked eye either as turbidity or in the form of a color change when SYBR Green I, a fluorescent dsDNA intercalating dye, is employed. LAMP does not require a thermal cycler and can be performed simply with a heating block and/or water bath. Additional discussion regarding LAMP can be found in "Loop mediated isothermal amplification (LAMP): a new generation of innovative gene amplification technique; perspectives in clinical diagnosis of infectious diseases" by Parida et al. Rev. Med. Virol. 2008; 18: 407-421.

In one embodiment, the plurality of primer strands includes at least one of a forward primer or a reverse primer for amplifying the sequence of interest.

In one embodiment, the method further includes sealing the fluid transport channel so as to prevent evaporation of the fluid in the sample wells. Sealing can include overlaying the sample wells with an oil or another thermostable, immiscible fluid that is added to the fluid transport channel after the reaction solution is loaded into the sample wells. Sealing can also be by physically capping the inlet and outlet ports.

Preferably, the concentration of nucleic acid template is selected such that the number of copies of the nucleic acid template in the reaction mixture that is loaded into the microfluidic flow cell is less than the number of sample wells so that, on average, the bulk of the sample wells have either zero copies of the nucleic acid template or one copy of the nucleic acid template with a small number of cells having two or more copies of the nucleic acid template. As such, the nucleic acid template is provided at a concentration such that the plurality of sample wells contain an average of about 0.1 copies of the nucleic acid template per sample well to about 1 copy of the nucleic acid template per sample well. More preferably, the concentration of the nucleic acid template is such that the plurality of sample wells contain an average of about 0.2 copies of the nucleic acid template per sample well to about 0.8 copies of the nucleic acid template per sample well. Most preferably, the concentration of the nucleic acid template is such that the plurality of sample wells contain an average of about 0.3 copies of the nucleic acid template per sample well to about 0.5 copies of nucleic acid template per sample well.

In one embodiment, the nucleic acid template can be from a diploid organism. In such a situation, the nucleic acid template is preferably provided at a concentration such that the plurality of sample wells contain no more than one copy of the organism's two copies of the sequence of interest.

Figure 5:
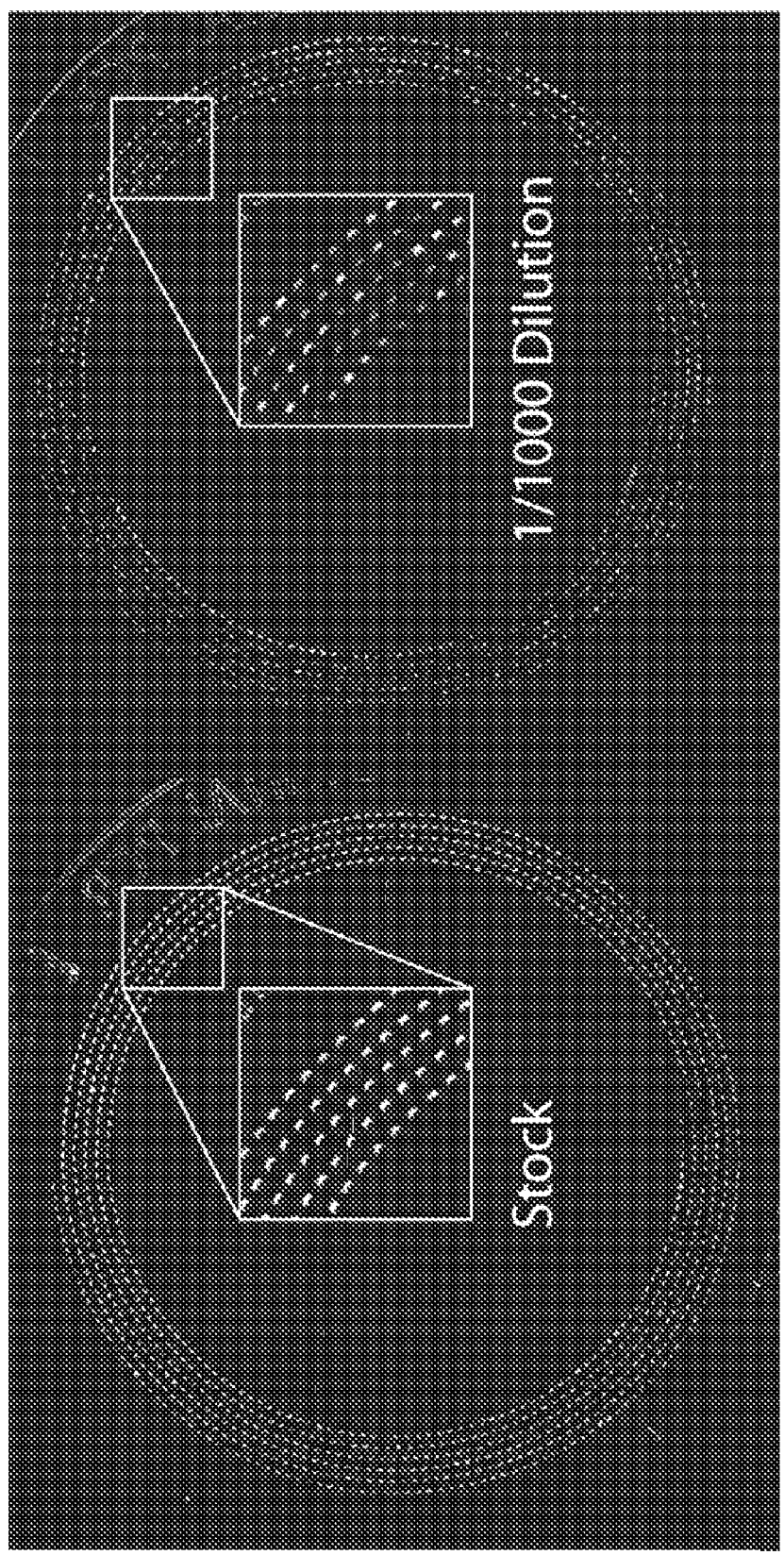
FIG. 5 illustrates a PCR experiment comparing a disc-shaped microfluidic cell filled using a concentrated nucleic acid template solution and a separate disc-shaped microfluidic cell using a diluted nucleic acid template solution.

FIG. 5 illustrates a PCR experiment comparing a disc-shaped microfluidic cell filled using a concentrated DNA template solution (Stock) and a separate disc-shaped microfluidic cell using a diluted DNA template solution (1:1000 Dilution). PCR solution with the dye LCGreen® Plus was pipetted into an inlet port towards the center of the disc and then spun at 3000 rpm to load each well. A modified air thermal cycler was used for PCR amplification (40 cycles in 16 minutes) and the disc was interrogated using a CCD camera image to determine how many wells fluoresce for quantification.

FIG. 5 shows amplified PCR product in each of the sample wells in the microfluidic cell filled using the concentrated DNA template solution (i.e., Stock). In contrast, amplified PCR product is only present in only a subset of sample wells in the microfluidic cell filled using the diluted DNA template solution (i.e., 1:1000 Dilution). This can be seen by comparing wells showing bright fluorescence with those showing only background fluorescence. The results shown in FIG. 5 demonstrate that single DNA molecule detection is possible with target dilution down to less than an average of 1 copy/well.

In one embodiment, the method further includes providing a microfluidic flow cell formed from a material having an affinity for the nucleic acid template such that the nucleic acid template is progressively diluted as it flows through the fluid transport channel from the inlet port toward the outlet port, and plotting a frequency of sample wells having amplified product versus sample wells having no amplified product as a function of distance along the fluid transport channel so as to find a subset of sample wells having a concentration of the nucleic acid template usable for DNA quantification.

Suitable examples of applications where DNA quantification can be used with the method described herein include, but are not limited to, at least one of cancer detection, cancer therapy response monitoring, quantification of viral load, prenatal genetic testing, and direct haplotyping.

In one embodiment, the DNA quantification can further include performing melting analysis on the amplified product. Melting analysis can include raising the temperature of the microfluidic flow cell and the contents therein, and monitoring the absorbance and/or fluorescence in each of the sample wells while raising the temperature to generate a melting profile for the amplified product, wherein a change in absorbance and/or fluorescence indicates denaturation of double stranded nucleic acids.

In one embodiment, the method can further include analyzing the results of the melting analysis, wherein a shift in the melting profile of the amplified product indicates the presence of sequence variants in the nucleic acid template.

In one embodiment, DNA melting analysis can be facilitated by including a plurality of DNA probe strands that are capable of forming a double stranded DNA structure with the sequence of interest and/or a fluorescent dye that fluoresces in the presence of double-stranded DNA.

In one embodiment, the method can further include providing a light source that can be positioned and timed for providing light at a fluorescence excitation wavelength to at least one sample well, flashing the light source at the fluorescence excitation wavelength so as to excite fluorescent emission from the fluorescent dye in the at least one sample well, and detecting the fluorescent emission from the fluorescent dye in the at least one sample well using a positionable detector means, wherein flashing the light source prevents photobleaching of the fluorescent dye in the sample well.

Figure 6:
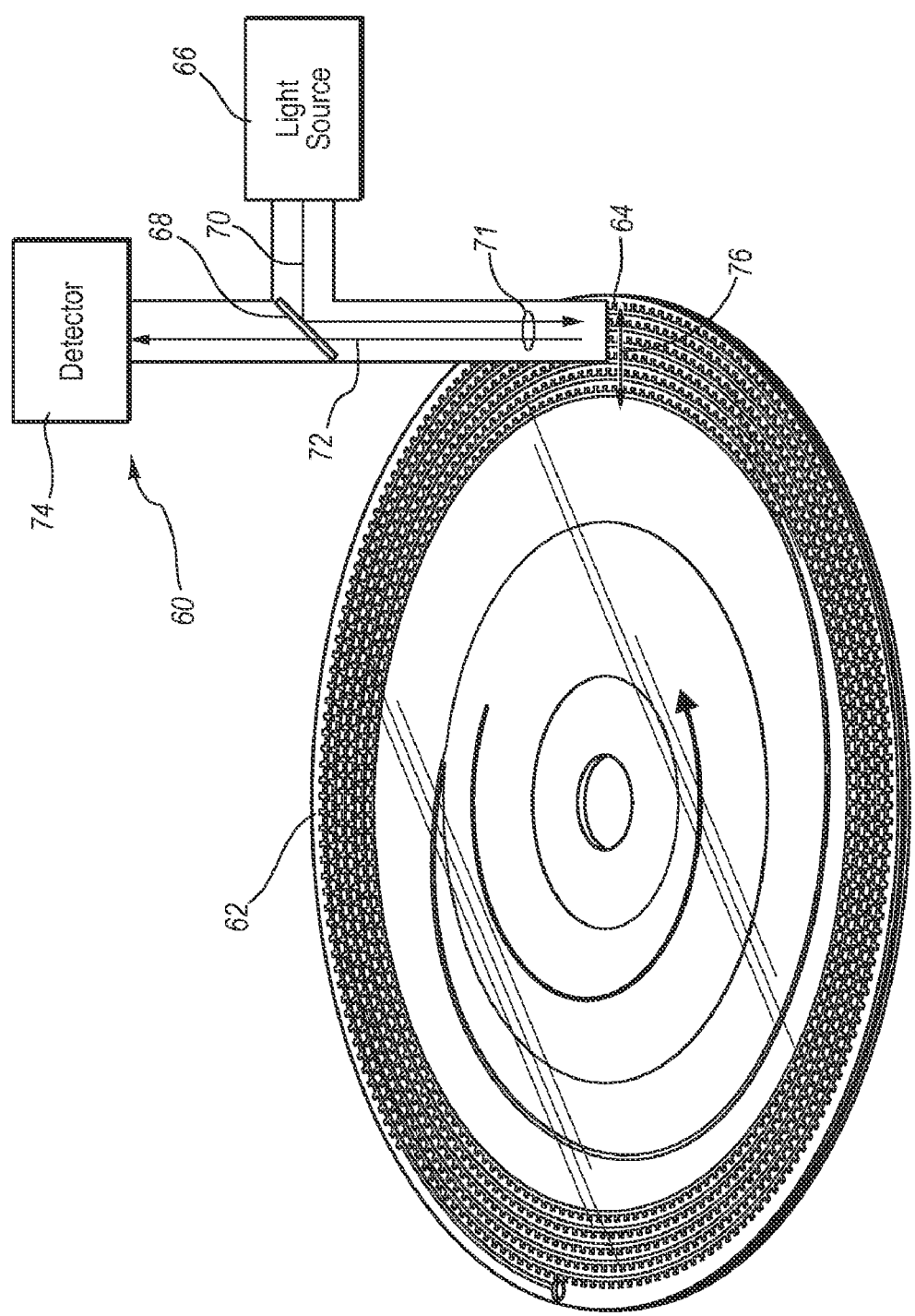
FIG. 6 illustrates an optical scanner according to one embodiment of the present invention.

FIG. 6 illustrates an optical scanner 60 that can be used to scan a rotating disc-shaped microfluidic cell 62 according to one embodiment of the present invention. The optical scanner includes a light source 66, a dichroic mirror assembly 68, focusing optics 71, and a detector 74. In the embodiment shown, the dichroic mirror assembly reflects and directs light at the excitation wavelength 70 while passing light at the fluorescent emission wavelength 72. In practice, the optical scanner 60 can be positioned 76 over the spinning optical disc 62. With the optical scanner in position, the light source 66 can be timed to flash in order to excite fluorescent emission from a selected sample well 64. Alternatively, light source 66 can be left on continuously. Light at the excitation wavelength 70 is produced by the light source, reflected by the mirror assembly 68, and focused onto a selected well 64 by the focusing optics 71. Fluorescent emission 72 from the selected sample well 64 by the focusing optics 71, and passed by the mirror assembly 68 into the detector. One will appreciate that a similar apparatus having a detector below the disc could be used to observe absorbance in a selected sample well.

EXAMPLES

Example 1

DNA Haplotyping

A haplotype, a contraction of the phrase "haploid genotype," is a set of closely linked genetic markers present on one chromosome which tend to be inherited together (not easily separable by recombination). Another way to think about it is that a haplotype is half of a genotype.

It is known that an organism's genotype may not uniquely define its haplotype. For example, consider a diploid organism and two bi-allelic loci on the same chromosome such as single nucleotide polymorphisms (SNPs). The first locus has alleles A and T with three possible genotypes AA, AT, and TT, the second locus having G and C, again giving three possible genotypes GG, GC, and CC. For a given individual, there are therefore nine possible configurations for the genotypes at these two loci, as shown in the Table 1 square below, which shows the possible genotypes that an individual may carry and the corresponding haplotypes that these resolve to. For individuals that are homozygous at one or both loci, it is clear what the haplotypes are; it is only when an individual is heterozygous at both loci that the phase is ambiguous.

TABLE 1

|    | AA    | AT              | TT    |
|----|-------|-----------------|-------|
| GG | AG AG | AG TG           | TG TG |
| GC | AG AC | AG TC<br>or<br>AC TG | TG TC |
| CC | AC AC | AC TC           | TC TC |

When multiple polymorphisms are heterozygous in the same gene, it is important to know the phase of the polymorphisms, that is, which alleles go together on the same chromosome. As is made clear in Table 1, this is not apparent from genotyping individual loci, but does define the structure and function of the gene product. Such "haplotyping" can typically be performed by family pedigree charts, cloning (Martinez-Arias et al. 2002), FRET hybridization probes if the distance between loci is small (Pont-Kingdon et al. 2005), complex software packages (Stephens et al. 2001), extensive dilutions (Paul and Apgar 2005), or procedures to separate out or tease apart the two different gene copies (Yan et al. 2000 and Douglas et al. 2001). However, these methods can give ambiguous results and they can be expensive and time consuming.

The microfluidic flow cell described herein provides an alternative method for haplotyping. The microfluidic flow cell uses an inexpensive rotating disc platform to partition a sample into a plurality of sample wells (e.g., a thousand or more sample wells) having a volume in a range from about 1 nl to about 100 nl. Concentration of DNA template is selected such that no sample well has more than one copy of the template DNA. This means that individual chromosomes can easily be separated from a stock of template DNA that includes both copies of the chromosome. Because individual chromosomes are in individual wells, separate copies of a sequence of interest can be amplified and probed for inter-chromosomal sequence variation.

Selected Genetic Loci

Warfarin is one of the most widely used coumadin anticoagulants but has a wide inter-individual dosage variation. Variants in the VKORC1 and CYP2C9 genes and certain environmental conditions (i.e. age, bodyweight and drug interactions) account for about 50-60% of the variation in warfarin dosage (Sconce et al. 2005 and Wadelius et al. 2007). Warfarin functions by interfering with vitamin K recycling in the liver. VKORC1 encodes for the main protein in the vitamin K epoxide reductase complex. Warfarin is metabolized by cytochrome P450 2C9 (CYP2C9). Thus, CYP2C9*2 and *3 alleles require lower warfarin doses and may have a greater risk of bleeding (Sanderson et al. 2005).

Mutations within the CFTR gene have been found to cause cystic fibrosis, a disease that causes the body to produce thick, sticky mucus which causes difficulty breathing and insufficient enzyme production in the pancreas. This disease is one of the most common autosomal recessive genetic disorders among the Caucasian population, affecting approximately 1 in 3,300 with a carrier rate of 1 in 29 (Heaney et al. 2006). A 3-bp deletion (delta F508 deletion) within this gene is the most common genetic marker for this disease (Riordan et al. 1989). Two other mutations, R117H in exon 4 and IVS-8 5T polymorphism in intron 8, when combined on the same chromosome (in cis) increases the severity of cystic fibrosis (Kiesewetter et al. 1993). Therefore, if an individual is heterozygous for both R117H and IVS-8 5T a direct haplotyping approach for cis/trans evaluation is needed (Pont-Kingdon et al. 2004), thus avoiding family studies which can be time consuming and more costly in a clinical setting.

Ataxia-telangiectasia is an autosomal recessive disorder which may include cerebellar degeneration, immunodeficiency, chromosomal instability, radiosensitivity and a predisposition for cancer (Platzer et al. 1997). This disorder occurs in about 1 in 40,000 to 1 in 100,000 people worldwide and the gene responsible is ATM (Palau and Espinós et al. 2006).

Hemochromatosis is an autosomal recessive disorder of iron metabolism causing the body to accumulate iron and affects approximately 1 in 400 individuals. This excess iron can lead to failure of a variety of organs and can also cause cirrhosis, hepatomas, diabetes, cardiomyopathy and arthritis (Feder et al. 1996). The major gene leading to hemochromatosis is HFE.

Nanoliter DNA Melting Analysis

Solution-phase, homogeneous DNA melting analysis for heterozygote scanning and single nucleotide polymorphism (SNP) genotyping was performed in 10 nl and 1 nl volumes on a custom microchip. Human genomic DNA was PCR amplified, using a LightCycler® thermocycler (Roche Applied Science, Indianapolis, Ind.), in the presence of the saturating fluorescent dye, LCGreen® Plus (Idaho Technology, SLC, Utah), and placed within microfluidic channels that were created between two glass slides using a double sided tape patterned by xurography (Bartholomeusz et al. 2005). The microchip was heated at 0.1° C./s with a Peltier device and viewed with an inverted fluorescence microscope modified for photomultiplier tube detection. The melting data was normalized and the negative first derivative plotted against temperature.

Mutation scanning for heterozygotes was easily performed by comparing the shape of the melting curve to homozygous standards. Genotyping of homozygotes by melting temperature (Tm) required absolute temperature comparisons. Mutation scanning of ATM exon 17 and CFTR exon 10 identified single base change heterozygotes in 84 and 193 base-pair (bp) products, respectively. All genotypes at HFE C282Y were distinguished by simple melting analysis of a 40-bp fragment.

Sequential analysis of the same sample on the gold-standard, commercial high-resolution melting instrument HR-1™ (Idaho Technology), followed by melting in a 10 nl or 1 nl reaction chamber, produced similar results. DNA melting analysis requires only minutes after PCR and is a simple method for genotyping and scanning that can be reduced to nanoliter volumes. Microscale systems for performing DNA melting reduce the reagents/DNA template required with a promise for high throughput analysis in a closed chamber without risk of contamination (Sundberg et al. 2007).

Array nanoliter DNA melting analysis with unlabeled probes and asymmetric PCR

Xurography was used to create a poly(dimethylsiloxane) (PDMS) (McDonald et al. 2000) soft lithography mold, with analysis wells being 1.125 mm in diameter and 0.1 mm in height, creating a 100 nl volume. PDMS was then molded and cured in an oven. PDMS ports were cored and then bonded to glass slide substrates using corona discharge. A Peltier heater (HT4-6-21x43, Melcor, Trenton, N.J.) and J-type thermocouple were used for temperature control. Detection used a CCD camera (iXon, Andor Technology, South Windsor, Conn.) cooled to −80° C. LEDs (440-460 nm, LXHL-BR02, LUXEON, Philips Lumileds Lighting Company, San Jose, Calif.) were filtered by an excitation bandpass filter (426-450 nm, Brightline Fluorescent Filters, Semrock, Rochester, N.Y.). Emitted light was collected by a lens (EFS 60 mm f/2.8 Macro, Canon, Lake Success, N.Y.) and passed through an emission filter (467-499 nm, Brightline Fluorescent Filters, Semrock). All hardware was controlled using LabView 8.0 (NI, Austin, Tex.). 10× asymmetric PCR with unlabeled oligonucleotide probes was performed on the DNA sample using a LightCycler® and then transferred to an HR-1™ instrument for a high-resolution reference melting curve. 2 µl of the amplified sample was pipetted into the microchip for nanoliter melting analysis. All three genotypes were melted simultaneously and each genotype had three wells for repeat analysis.

The 100 nl melts are in good agreement with the 10 µl HR-1 melt curves and each of the genotypes clearly clustered together using an agglomerative, unbiased hierarchical clustering of melting curves (Duda et al. 2001) to make the calls. Given n curves, the two curves that are closest to each other are first determined. The distance between a pair of curves is taken as the mean absolute value of the fluorescence differences between the curves over all temperature acquisitions. The closest two curves are deleted and replaced by their mean, resulting in a new set of n−1 curves. The next nearest pair is then replaced by the weighted mean of that pair. At each step, the weight is the number of original curves that make up each branch being averaged. This process is performed a total of n−1 times until the last pair of curves is merged, producing a dendrogram showing the most likely clusters at each level. The process does not determine the number of clusters (i.e. the number of genotypes) represented by the n curves but does confirm appropriate clustering of samples at each dendrogram level. For these tests three clusters were chosen to represent each of the three genotypes.

This new platform provides accurate SNP genotyping capability using a hundredth of the volume currently used with gold-standard instrumentation. This technology with further development will lead to more accurate warfarin dosing within the clinical setting.

Example 2

Cancer Detection and Cancer Therapy Response Monitoring

Current cancer detection imaging techniques (i.e. NMR, X-ray and CT scans) are able to detect tumors only after they approach macroscopic size, which in many cases may be too late for effective treatment. Invasive biopsy sampling is also required. Metabolic screens for some tumors exist but only provide indirect evidence. The detection process is illustrated with the following example.

Lung cancer patients are often not checked by a doctor until symptoms start to occur, such as wheezing, coughing up blood, chest pain and shortness of breath. These symptoms can be caused by the presence of a tumor in the lung putting pressure on the chest. The doctor will then order X-rays and CT scans and if the images come back positive then a biopsy is used to confirm that the tumor is cancerous. The biopsy is obtained by either bronchoscopy, inserting a needle into the lung, or surgery. If the biopsy is cancerous then the doctor will determine the stage of the tumor and best treatment options. Patients with stage I cancer have a 50 percent chance of surviving past 5 years. However, the survival rate rapidly declines for stages II, III, and IV. The 5-year survival rate for stage IV is only 2 percent.

The microfluid flow cell described herein can be used with digital PCR to detect cancerous tumors much earlier from a blood, urine, sputum, or stool sample. In essence this allows one to find the proverbial "needle in a haystack". As the tumor grows it sheds minute amounts of cancerous cells into the body. Since cancer is a genetic disease, cancer cells have signature sequence variants (depending on the tumor type and particular individual tumor) that can be detected in amplified PCR products by probe or melting analysis. The system described herein is able to detect these variants, providing both detection and quantification of cancerous cells. For example, mutations in tumor suppressor genes such as BRCA1 and TP53, and oncogenes such as c-kit, k-ras, and EGFR are found in many tumors.

Cancer therapy response monitoring can also be performed using the microfluidic flow cell described herein in a similar manner. Whether or not a treatment is successful can be monitored by analyzing blood, urine, sputum, or stool samples over time to determine whether the numbers of cancerous cells are increasing, staying the same, or decreasing.

Example 3

Quantification of Viral Load

Viral load can be quantified in a sample (e.g., blood or urine) by using the microfluidic cell described herein. Viral DNA or RNA from a sample is partitioned into a large number of sample wells in the microfluidic flow cell and the viral sequences are amplified and detected by fluorescent probes or dyes. Viral load can be estimated by determining the dilution factor from the sample necessary to achieve a situation where the sample wells have, on average, less than one copy of viral template per well. Because viral load is unknown, it is particularly appropriate to use a microfluidic flow cell fabricated from a material having affinity for nucleic acid (e.g., PETG) in this application. Since the dilution of the template DNA along the flow path is determined by the affinity of the disc material to nucleic acid and the geometric configuration of channels, the dilution of template along the path is a constant for any particular disc type and can be used to calculate exact template concentrations. For example, each disc type can be calibrated to correlate the path length where the fraction of positive wells is 50% to the template concentration in the original solution. Such a calibration produces a standard curve that relates quantitative viral load to the path length position where the on/off frequency is 50%, an easily determined parameter by plotting the frequency of wells that are positive vs path length.

Example 4

Prenatal Genetic Testing

Prenatal genetic testing is very similar to cancer detection. As the fetus grows in its mother's uterus, small amounts of fetal DNA is shed into the mother's blood. Genetic disease in the fetus correlates with genetic changes that can be detected in this cell free DNA, estimated to be about 5% of circulating DNA in the maternal circulation. The system described herein allows mutations in this fetal DNA to be identified by probe or melting analysis.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A microfluidic flow cell, comprising:
   a body having a fluid transport channel disposed therein, the fluid transport channel having a proximal end and a distal end defining a fluid flow path;
   a fluid inlet port disposed at the proximal end of the fluid transport channel at a central portion of the body and an outlet port disposed at the distal end of the fluid transport channel at an outer portion of the body; and
   a plurality of sample wells in direct fluid communication with the fluid transport channel and substantially perpendicular to the fluid flow path in the fluid transport channel such that a volume of a liquid medium flowing through the fluid transport channel will flow into at least a first sample well with an excess of the liquid medium flowing into at least a second sample well.

2. The microfluidic flow cell as recited in claim 1, each of the sample wells having a volume between about 1 nl and about 100 nl.

3. The microfluidic flow cell as recited in claim 1, each of the sample wells having a volume between about 10 nl and about 80 nl.

4. The microfluidic flow cell as recited in claim 1, each of the sample wells having a volume between about 20 nl and about 50 nl.

5. The microfluidic flow cell as recited in claim 1, the body further comprising at least first and second outer layers and an inner layer disposed between the first and second outer layers;
the fluid transport channel being formed in the inner layer; and
the fluid inlet and the fluid outlet ports being disposed in the first or second outer layers.

6. The microfluidic flow cell as recited in claim 5, the fluid inlet port being disposed in the first outer layer and the fluid outlet port being disposed in the second outer layer.

7. The microfluidic flow cell as recited in claim 1, the body further comprising at least a first layer and a second layer;
the fluid transport channel being formed in the second layer;
the first layer being disposed over the second layer and over the fluid transport channel; and
the fluid inlet and the fluid outlet ports being disposed in the first or second layers.

8. The microfluidic flow cell as recited in claim 7, the fluid inlet port being disposed in the first layer and the fluid outlet port being disposed in the second layer.

9. The microfluidic flow cell as recited in claim 1, the body being a rotatable disc such that a fluid applied at the inlet port will flow through the fluid path toward the outlet port when the disc is rotated.

10. A microfluidic flow cell, comprising:
a disc-shaped body configured for spinning about a central axis, the body further including:
at least one fluid inlet port situated toward a center portion of the disc and at least one fluid outlet port situated toward an outer edge of the disc;
at least one fluid transport channel defining a fluid flow path in the body, the fluid transport channel being disposed in the body such that it is in fluid communication with a fluid inlet port and a fluid outlet port; and
a plurality of sample wells in direct fluid communication with the at least one fluid transport channel such that the sample wells are substantially perpendicular to the fluid flow path, wherein a fluid applied at the inlet port will flow through the body along the fluid path toward the outlet port in response to spinning the disc-shaped body about the central axis.

11. The microfluidic flow cell as recited in claim 10, each of the sample wells having a volume between about 20 nl and about 50 nl.

12. The microfluidic flow cell as recited in claim 10, the body further comprising at least first and second outer layers and an inner layer disposed between the first and second outer layers;
the fluid transport channel being formed in the inner layer;
the fluid inlet port being disposed in the first outer layer; and
the fluid outlet port being disposed in the first outer layer or the second outer layer.

13. The microfluidic flow cell as recited in claim 12, the fluid inlet port being disposed in the first outer layer and the fluid outlet port being disposed in the second outer layer.

14. The microfluidic flow cell as recited in claim 10, the body further comprising at least a first layer and a second layer;
the fluid transport channel being formed in the second layer;
the first layer being disposed over the second layer and over the fluid transport channel; and
the fluid inlet port being disposed in the first layer; and
the fluid outlet port being disposed in the first layer or the second layer.

15. The microfluidic flow cell as recited in claim 14, the fluid inlet port being disposed in the first layer and the fluid outlet port being disposed in the second layer.

16. The microfluidic flow cell as recited in claim 10, the body further comprising:
a plurality of inlet ports situated toward the center of the disc;
a plurality of outlet ports situated toward the outer edge of the disc; and
a plurality of fluid transport channels for transporting a flowable fluid with each channel being connected to one inlet port and one outlet port.

17. A method for filling a microfluidic flow cell, comprising:
providing a microfluidic flow cell as recited in one of claim 1 or claim 10;
applying a volume of a flowable fluid to the fluid inlet port; and
flowing the flowable fluid through the fluid transport channel toward the fluid outlet port such that the flowable fluid will flow into at least a first sample well with an excess of the flowable fluid flowing into at least a second sample well.

18. The method as recited in claim 17, the flowing further comprising spinning the flow cell about its central axis in a centrifuge so as to cause the flowable fluid to flow from the fluid inlet port, through the fluid transport channel, and toward the fluid outlet port.

19. The method as recited in claim 18, further comprising spinning the flow cell at a rate between about 500 rpm and about 10,000 rpm.

20. The method as recited in claim 18, further comprising spinning the flow cell at a rate between about 2000 rpm and about 8000 rpm.

21. The method as recited in claim 18, further comprising spinning the flow cell at a rate between about 3000 rpm and about 5000 rpm.

22. The method as recited in claim 17, wherein the volume of flowable fluid that is applied to the inlet port is sufficient to fill each of the plurality of samples well that are disposed in the fluid transport channel, and wherein excess flowable fluid flows out of the fluid transport channel through the fluid outlet port.

23. The method as recited in claim 22, wherein the filled sample wells are not in fluid communication with adjacent filled sample wells.

24. A method for manufacturing a microfluidic flow cell, comprising:
providing a fluid transport layer, comprising;
forming a fluid transport channel defining a fluid flow path in the fluid transport layer, the fluid transport channel having a proximal end at a central portion of the fluid transport layer and a distal end at an outer portion of the fluid transport layer;
forming a plurality sample wells in direct fluid communication with the fluid transport channel, the plurality sample wells being substantially perpendicular to the fluid flow path in the fluid transport channel; and sealing the fluid transport layer with at least one outer layer.

25. The method as recited in claim 24, the forming including at least one of xurography, lithography and etching, laser cutting, stamping, hot embossing, injection molding, and micro machining.

26. The method as recited in claim 24, each of the sample wells having a volume between about 1 nl and about 100 nl.

27. The method as recited in claim 24, the fluid transport layer being formed from a polymeric, thermoplastic material.

28. The method as recited in claim 24, the fluid transport layer being formed from a glass material.

29. The method as recited in claim 24, the fluid transport layer being formed from an inert material.

30. The method as recited in claim 24, the fluid transport layer being formed from a material having an affinity for DNA and/or protein.

31. The method as recited in claim 24, further comprising:
disposing an outer layer over the fluid transport layer, the outer layer including at least inlet and outlet ports that are in fluid communication with the fluid transport channel.

32. The method as recited in claim 24, further comprising:
disposing the fluid transport layer between the first and second outer layers, the first and second outer layers including at least inlet and outlet ports that are in fluid communication with the fluid transport channel.

33. A method for DNA quantification, comprising:
providing a microfluidic flow cell as recited in one of claim 1 or claim 10;
loading the plurality of sample wells in the microfluidic flow cell with a reaction mixture, the reaction mixture including a nucleic acid template, a plurality of primer strands for amplifying a sequence of interest, and means for amplifying the nucleic acid template;
amplifying the nucleic acid template to generate an amplified product therefrom;
detecting the presence or absence of the amplified product in a plurality of wells; and
quantifying the amount of the nucleic acid template amplified.

34. The method as recited in claim 33, wherein means for amplifying the nucleic acid template include at least one of polymerase chain reaction (PCR), ligase chain reaction (LCR), transcription mediated amplification (TMA), rolling circle amplification (RCA), strand displacement amplification (SDA), or loop-mediated amplification (LAMP).

35. The method as recited in claim 33, wherein the plurality of primer strands includes at least one of a forward primer or a reverse primer for amplifying the sequence of interest.

36. The method as recited in claim 33, further comprising sealing the fluid transport channel so as to prevent evaporation of the fluid in the sample wells.

37. The method as recited in claim 33, each of the sample wells in the flow cell having a volume between about 1 nl and about 100 nl.

38. The method as recited in claim 33, wherein the nucleic acid template is provided at a concentration such that the plurality of sample wells contain an average of about 0.1 copies of the nucleic acid template per sample well to about 1 copy of the nucleic acid template per sample well.

39. The method as recited in claim 33, wherein the nucleic acid template is provided at a concentration such that the plurality of sample wells contain an average of about 0.2 copies of the nucleic acid template per sample well to about 0.8 copies of the nucleic acid template per sample well.

40. The method as recited in claim 33, wherein the nucleic acid template is provided at a concentration such that the plurality of sample wells contain an average of about 0.3 copies of the nucleic acid template per sample well to about 0.5 copies of the nucleic acid template per sample well.

41. The method as recited in claim 33, further comprising:
providing the nucleic acid template from a diploid organism at a concentration such that each of the plurality of sample wells contain no more than one copy of the organism's two copies of the sequence of interest.

42. The method as recited in claim 33, further comprising:
providing a microfluidic flow cell formed from a material having an affinity for the nucleic acid template such that the nucleic acid template is progressively diluted as it flows down the fluid transport channel; and
plotting a frequency of sample wells having amplified product versus sample wells having no amplified product as a function of distance along the fluid transport channel so as to find a subset of sample wells having a concentration of the nucleic acid template usable for quantification.

43. The method as recited in claim 33, wherein quantifying the amount of the nucleic acid template amplified provides for at least one of cancer detection, cancer therapy response monitoring, quantification of viral load, prenatal genetic testing, or direct haplotyping.

44. The method as recited in claim 33, wherein quantifying the amount of the nucleic acid template amplified further comprises:
performing melting analysis on the amplified product, the melting analysis including:
raising the temperature of the microfluidic flow cell and the contents therein; and
monitoring the absorbance and/or fluorescence in each of the sample wells while raising the temperature to generate a melting profile for the amplified product, wherein a change in absorbance and/or fluorescence indicates denaturation of a double stranded nucleic acid.

45. The method as recited in claim 44, further comprising analyzing the results of the melting analysis, wherein a shift in the melting profile of the amplified product indicates the presence of sequence variants in the nucleic acid template.

46. The method as recited in claim 44, the reaction mixture further comprising a plurality of DNA probe strands that are capable of forming a double stranded DNA structure with the sequence of interest and/or a fluorescent dye that fluoresces in the presence of double-stranded DNA.

47. The method as recited in claim 46, further comprising:
providing a light source that is positionable and timeable for providing light at a fluorescence excitation wavelength to at least one sample well;
flashing the light source at the fluorescence excitation wavelength so as to excite fluorescent emission from the fluorescent dye in the at least one sample well; and
detecting the fluorescent emission from the fluorescent dye in the at least one sample well using a positionable detector means,
wherein flashing the light source substantially prevents photobleaching of the fluorescent dye in the sample well.

* * * * *